United States Patent
Molino et al.

(10) Patent No.: US 7,956,090 B2
(45) Date of Patent: *Jun. 7, 2011

(54) COMPOSITION AND METHOD FOR INCREASING THE ANABOLIC STATE OF MUSCLE CELLS

(76) Inventors: Michele Molino, Oakdale, CA (US); Joseph MacDougall, Oakdale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/499,109

(22) Filed: Jul. 8, 2009

(65) Prior Publication Data

US 2009/0270501 A1 Oct. 29, 2009

Related U.S. Application Data

(63) Continuation of application No. 11/853,277, filed on Sep. 11, 2007, now Pat. No. 7,645,794.

(51) Int. Cl.
*A61K 31/225* (2006.01)
*A61K 31/20* (2006.01)
(52) U.S. Cl. ........................ 514/547; 514/560
(58) Field of Classification Search ................. 514/547, 514/560

See application file for complete search history.

(56) References Cited

U.S. PATENT DOCUMENTS 7,645,794 B2 * 1/2010 Molino et al. ................. 514/547
2005/0059738 A1 3/2005 Ajami et al.

FOREIGN PATENT DOCUMENTS

WO 9804254 2/1998

OTHER PUBLICATIONS

Brooks GA. Mammalian fuel utilization during sustained exercise. Comp Biochem Physiol B Biochem Mol Biol. May 1998;120(1):89-107.
Kirkwood SP, Munn EA, Brooks GA. Mitochondrial reticulum in limb skeletal muscle. Am J Physiol. Sep. 1986;251(3 Pt 1):C395-402.
Robergs R, Ghiasvand F, Parker D. Biochemistry of exercise-induced metabolic acidosis. Am J Physiol Regul Integr Comp Physiol. 2004;287:R502-16.
Rennie MJ. Body maintenance and repair: how food and exercise keep the musculoskeletal system in good shape. Exp Physiol. Jul. 2005;90(4):427-36.
Smith K, Reynolds N, Downie S, Patel A, Rennie MJ. Effects of flooding amino acids on incorporation of labeled amino acids into human muscle protein. Am J Physiol. Jul. 1998;275(1 Pt 1):E73-8.
Matthews DE. Observations of branched-chain amino acid administration in humans. J Nutr. Jun. 2005;135(6 Suppl): 1580S-4S.
Brand KA, Hermfisse U. Aerobic glycolysis by proliferating cells: a protective strategy against reactive oxygen species. FASEB J. Apr. 1997;11(5):388-95.
Sappington PL, Han X, Yang R, Delude RL, Fink MP. Ethyl pyruvate ameliorates intestinal epithelial barrier dysfunction in endotoxemic mice and immunostimulate caco-2 enterocytic monolayers. J Pharmacol Exp Ther. Jan. 2003;304(1): 464-76.
Montgomery CM, Webb JL. Metabolic studies on heart mitochondria. II. The inhibitory action of parapyruvate on the tricarboxylic acid cycle. J Biol Chem. Jul. 1956;221(1):359-68.
Butz CE, McClelland GB, Brooks GA. MCT1 confirmed in rat striated muscle mitochondria. J Appl Physiol. Sep. 2004; 97(3):1059-66.
Roth DA, Brooks GA. Lactate and pyruvate transport is dominated by a pH gradient-sensitive carrier in rat skeletal muscle sarcolemmal vesicles. Arch Biochem Biophys. Jun. 1990;279(2):386-94.
Boebek KP, Baker DH. Comparative utilization of the alpha-keto and D- and L-alpha-hydroxy analogs of Leucine, Isoleucine and Valine by chicks and rats. J Nutr. Oct. 1982;112(10):1929-39.
Karila T, Seppala T. Alpha-hydroxyisocaproic acid (HICA)—a Leucine metabolite for muscle recovery following exercise. From supplier www.elmomed.com.
Staten MA, Bier DM Matthews DE. Regulation of valine metabolism in man: a stable isotope study. Am J Clin Nutr. Dec. 1984;40(6):1224-34.
Hoffer LJ, Taveroff A, Robitaille L, Mame OA, Reimer ML. Alpha-keto and alpha-hydroxy branched-chain amino acid interrelationships in normal humans. J Nutr. Sep. 1993;123(9):1513-21.
Tischler ME, Desautels M, Goldberg AL. Does Leucine, leucyl-tRNA, or some metabolite of Leucine regulate protein synthesis and degradation in skeletal and cardiac muscle? J Biol Chem. Feb. 25, 1982;257(4):1613-21.
Bevilacqua L, Ramsey JJ, Hagopian K, Weindruch R, Harper ME. Effects of short- and medium-term calorie restriction on muslce mitochondrial proton leak and reactive oxygen species production. Am J Physiol Endocrinol Metab. May 2004;286(5):E852-61 (Abstract).
International Search Report for PCT/CA2007/001615 dated Jun. 4, 2008, International Filing Date: Sep. 11, 2007, Applicant: Multi Formulations Ltd. et al.
Yoshizawa, F: "Regulation of protein synthesis by branched-chain amino acids in vivo", Biochem Biophys Res Commun. Jan. 9, 2004;313(2):417-22.
Van Someren, KA et al.: "Supplementation with beta-hydroxy-beta-methylbutyrate (HMB) and alpha-ketoisocaproic acid (KIC) reduces signs and symptoms of exercise-induced muscle damage in man", Int J Sport Nutr Exerc Metab. Aug. 2005;15(4):413-24.

* cited by examiner

*Primary Examiner* — Raymond J Henley, III

(57) ABSTRACT

A nutritional supplement comprising at least a therapeutically effective amount of ethyl pyruvate and a therapeutically effective amount of at least one α-hydroxy branched-chain amino acid metabolite is provided by the present invention. The ingredients of the present nutritional supplement substantially simultaneously act to induce a anabolically-favorable state for muscle by substantially simultaneously maintaining blood and muscle physiological pH levels as well as increasing cellular concentrations of branched-chain amino acids. Both a composition and a method are provided by the present disclosure.

14 Claims, No Drawings

COMPOSITION AND METHOD FOR INCREASING THE ANABOLIC STATE OF MUSCLE CELLS

RELATED APPLICATIONS

This application is a continuation of, and claims the benefit of priority of, application U.S. patent application Ser. No. 11/853,277, entitled "Compositions and Methods for Increasing the Anabolic State of Muscle Cells," filed on Jun. 11, 2007, now issued as U.S. Pat. No. 7,645,794, which is hereby incorporated by reference in its entirety.

FIELD OF THE INVENTION

The present invention relates to a nutritional supplement for inducing an anabolically-favored state for muscle by substantially simultaneously maintaining blood and muscle physiological pH levels as well as increasing cellular concentrations of branched-chain amino acids. More specifically, the present invention relates to a nutritional supplement comprising a combination of ethyl pyruvate and α-hydroxyisocaproic acid (HICA).

BACKGROUND OF THE INVENTION

During intense periods of exercise, where the rate of demand for energy is high, pyruvate resulting from the breakdown of glucose is converted into lactate. This reduction of pyruvate to lactate is beneficial since it regenerates $NAD^+$ for the continuation of glycolytic energy production required by the working muscle. Increased lactate can be removed in a number of ways; it can be exported from the oxygen-deficient cell and taken up by an oxygen-rich cell where it can be oxidized to pyruvate and used directly to fuel the citric acid cycle (Brooks G A. Mammalian fuel utilization during sustained exercise. Comp Biochem Physiol B Biochem Mol Biol. 1998 May; 120(1):89-107. Review), or it can be reconverted by the liver, through the Cori cycle, to glucose.

The recognition of monocarboxylate transport (MCT) proteins in the mitochondria and the closely associated lactate oxidation complexes (Kirkwood S P, Munn E A, Brooks G A. Mitochondrial reticulum in limb skeletal muscle. Am J Physiol. 1986 September; 251(3 Pt 1):C395-402), suggests that lactate can be transported and oxidized in the mitochondria of the same cell.

Contrary to popular belief, increased levels of lactate do not directly cause acidosis; an elevated presence of acidic species (Robergs R, Ghiasvand F, Parker D. Biochemistry of exercise-induced metabolic acidosis. Am J Physiol Regul Integr Comp Physiol. 2004; 287:R502-16). Lactate appears to be a consequence rather then the cause of cellular events which cause acidosis. The physiological state of muscle cells are such that lactate never has hydrogen available to decrease pH in the surrounding solution. Acidosis is actually a result of the hydrolysis of ATP, wherein hydrogen ions are released into the surrounding solution. During heavy exercise, ATP is produced and utilized quickly in the cytoplasm causing a rapid decrease in cellular pH. The buffering systems of the tissues are rapidly overcome and pH drops resulting in a state of acidosis.

Additionally, several hours after exercise there are dynamic changes in the rates of both skeletal muscle synthesis and breakdown. The consumption of specific dietary components are known to further influence the response of skeletal muscle to exercise. The main components of food which are known to stimulate increased muscle protein synthesis are amino acids (Rennie M J. Body maintenance and repair: how food and exercise keep the musculoskeletal system in good shape. Exp Physiol. 2005 July; 90(4):427-36). Increased levels of circulating essential amino acids have been shown to stimulate protein synthesis (Smith K, Reynolds N, Downie S, Patel A, Rennie M J. Effects of flooding amino acids on incorporation of labeled amino acids into human muscle protein. Am J Physiol. 1998 July; 275(1 Pt 1):E73-8).

More specifically, the branched-chain amino acids (BCAA) consisting of Leucine, Isoleucine and Valine, are not only used for the synthesis of other amino acids, but are also important in the regulation of anabolic processes in muscle. Furthermore, BCAA not only increase the rate of protein synthesis but also inhibit the rate of protein degradation (Matthews D E. Observations of branched-chain amino acid administration in humans. J Nutr. 2005 June; 135(6 Suppl): 1580S-4S).

In situations following extended periods of repetitive, forceful muscular contractions, such as during exhaustive physical exercise, it would be advantageous for an individual to both maintain physiological pH levels and increase cellular concentrations of Leucine. In this regard, the anabolic state of muscle is increased, facilitating shorter recovery periods as well as increasing strength and muscle size.

SUMMARY OF THE INVENTION

The present invention is directed towards a nutritional supplement, comprising at least a therapeutically effective amount of ethyl pyruvate and a therapeutically effective amount of α-hydroxyisocaproic acid (HICA). The ingredients of the present nutritional supplement act to induce an anabolically-favored state in muscle by substantially simultaneously maintaining blood and muscle physiological pH levels as well as increasing cellular concentrations of Leucine. Both a composition and a method are provided by the present disclosure.

In additional aspects of the present invention the α-hydroxyisocaproic acid (HICA), may be replaced by other α-hydroxy branched-chain amino acid metabolites, such as α-hydroxy-β-methylvaleric acid (HIMVA), and α-hydroxy-isovaleric acid (HIVA), for example. Additionally, the composition of the present invention may include one or more of the α-hydroxyisocaproic acid (HICA), α-hydroxy-β-methylvaleric acid (HIMVA), and α-hydroxy-isovaleric acid (HIVA).

DETAILED DESCRIPTION OF THE INVENTION

In the following description, for the purposes of explanations, numerous specific details are set forth in order to provide a thorough understanding of the present invention. It will be apparent, however, to one of ordinary skill in the art that the present invention may be practiced without these specific details.

The present invention is directed towards a nutritional supplement, for inducing an anabolically-favored state in muscle by substantially simultaneously maintaining blood and muscle physiological pH levels as well as increasing cellular concentrations of Leucine.

As used herein, the term 'anabolic' is understood to represent metabolic processes where complex molecules are synthesized from more simple ones, i.e. synthesis of muscle proteins from amino acids. Additionally, as used herein, the term 'anabolic' also includes mechanisms of action which are anti-catabolic, such as destructive processes wherein the break down or larger molecules into smaller molecules occurs.

As used herein, 'α-hydroxyisocaproic acid' makes reference to the chemical 2-hydroxy-4-methylvaleric acid, (CAS Registry No. 498-36-2), also known as HICA, or leucic acid. Additionally, as used herein, the term 'α-hydroxyisocaproic acid' also includes derivatives of α-hydroxyisocaproic acid such as esters, and amides, and salts, as well as other derivatives, including derivatives having substantially similar pharmacoproperties to α-hydroxyisocaproic acid upon metabolism to an active form.

As used herein, the term 'α-hydroxy branched-chain amino acid metabolite' includes nitrogen-free metabolites of the branched-chain amino acids, Leucine, Isoleucine and Valine. More specifically, the term 'α-hydroxy branched-chain amino acid metabolite' refers to α-hydroxyisocaproic acid (HICA), α-hydroxy-β-methylvaleric acid (HIMVA), and α-hydroxy-isovaleric acid (HIVA).

A used herein, the term 'nutritional supplement' includes dietary supplements, diet supplements, nutritional compositions, supplemental dietary and other compositions similarly envisioned and termed not belonging to the conventional definition of pharmaceutical interventions as is known in the art. Furthermore, 'nutritional supplements' as disclosed herein belong to category of compositions having at least one physiological function when administered to a mammal by conventional routes of administration.

Ethyl Pyruvate

Pyruvate, or pyruvic acid, is a simple α-ketocarboxylate which is an important intermediate of glucose metabolism as well as being an endogenous antioxidant and free radical scavenger (Brand K A, Hermfisse U. Aerobic glycolysis by proliferating cells: a protective strategy against reactive oxygen species. FASEB J. 1997 April; 11(5):388-95). This recognition of pyruvate as an effective free radical scavenger prompted a surge of investigation for therapeutic uses.

However, a limitation with regard to the usefulness of pyruvate is its poor stability in aqueous solution (Sappington P L, Han X, Yang R, Delude R L, Fink M P. Ethyl pyruvate ameliorates intestinal epithelial barrier dysfunction in endotoxemic mice and immunostimulated caco-2 enterocytic monolayers. J Pharmacol Exp Ther. 2003 January; 304(1): 464-76). Upon dissolution in water pyruvate undergoes condensation and cyclization type reactions resulting in a variety of chemical species, some of which may be toxic (Montgomery C M, Webb J L. Metabolic studies on heart mitochondria. II. The inhibitory action of parapyruvate on the tricarboxylic acid cycle. J Biol Chem. 1956 July; 221(1):359-68). In order to overcome the shortcomings of pyruvate an ester derivative, ethyl pyruvate, was developed. Ethyl pyruvate will not undergo the condensation and cyclization type reactions in water because of the ester protecting group. Specific enzymes, such as esterases which are present in mammals are required for the removal of the ethyl ester. Thus the use of ethyl pyruvate enhances the uptake of pyruvate by reducing the potential for condensation and cyclization.

Pyruvate is endogenously produced in cells as a result of the metabolism of glucose by glycolysis. In situations where a cell has an adequate supply of oxygen the pyruvate is converted into acetyl-coenzyme A, transported into the mitochondria, and enters a series of reactions collectively known as the Krebs cycle. However, in situations of oxygen deficiency, often occurring in muscle as a result of extended periods of exercise, the pyruvate is converted into lactate. While pyruvate can be transported directly into the mitochondria, most of it is reduced to lactate in the cytosol, prior to transport. This reduction of pyruvate consumes a free proton from the cytoplasm and so acts as a buffer against acidosis (Robergs R, Ghiasvand F, Parker D. Biochemistry of exercise-induced metabolic acidosis. Am J Physiol Regul Integr Comp Physiol. 2004; 287:R502-16).

Lactate, resulting from the conversion of pyruvate, can be transported into the mitochondria where it can be oxidized (Butz C E, McClelland G B, Brooks G A. MCT1 confirmed in rat striated muscle mitochondria. J Appl Physiol. 2004 September; 97(3):1059-66), or it can be exported out of the cell and taken up by oxygen-rich muscle cells. The transport of lactate into the mitochondria is facilitated by MCT proteins, which are proton-linked transporters, i.e. protons are co-transported into the mitochondria with lactate (Roth D A, Brooks G A. Lactate and pyruvate transport is dominated by a pH gradient-sensitive carrier in rat skeletal muscle sarcolemmal vesicles. Arch Biochem Biophys. 1990 June:279 (2):386-94). Therefore, as cytostolic pH decreases as a result of ATP hydrolysis and cytostolic concentrations of lactate increase as a result of ethyl pyruvate administration, the co-transport of free protons and lactate out of the cytosol is increased.

It is herein understood by the inventors that inclusion of ethyl pyruvate in a nutritional supplement will increase cellular levels of pyruvate. This increased concentration of cellular pyruvate will facilitate greater conversion to lactate, thus greater consumption of free protons, and increased regeneration of $NAD^+$. The increased regeneration of $NAD^+$ will facilitate greater levels of glycolytic energy production required by the working muscle and the increased consumption of free cytosolic protons will buffer against acidosis resulting from the increased glycolytic energy production. Additionally, it is also understood by the inventors that increased levels of cytosolic lactate will increase the co-transport of protons and lactate into the mitochondria, thereby further buffering the cell against acidosis as well as increasing the substrate inside the mitochondria available to fuel the citric acid cycle.

In an embodiment of the present invention, which is set forth in greater detail in the examples below, the nutritional composition comprises ethyl pyruvate. A serving of the nutritional composition comprises from about 0.0001 g to about 0.75 g of ethyl pyruvate.

α-Hydroxyisocaproic Acid (HICA)

α-Hydroxyisocaproic acid is an end product of the metabolism of the branched chain amino acid, Leucine. Foods that are produced by fermentation, such as some cheeses, may contain small amounts of HICA. HICA is a reduction product of the α-keto acid analog of Leucine, α-ketoisocaproic acid (KICA), and as such contributes to the free pools of branched chain amino acids (BCAA). HICA belongs to the group collectively known as branched chain amino acid analogues.

Branched chain amino acid analogues are essentially nitrogen-free amino acids and may serve three roles in cases of nitrogen accumulation, 1) providing the dietary requirement of the corresponding branched-chain amino acid without increasing nitrogen intake; 2) reducing the amount of nitrogen that must be excreted from the body; and 3) increasing levels of Leucine, which plays a key role in protein turnover and prevents wasting of lean body mass. It is important to note that nitrogen accumulation can result from a number of situations including the catabolism of proteins in muscle during exercise.

Since branched chain amino acid analogues may be reaminated back to amino acid, e.g. HICA can be converted to KICA which can subsequently be converted back to Leucine, they can act to provide the dietary requirements for BCAA without increasing level of ingested nitrogen (Boebek K P, Baker D H. Comparative utilization of the α-keto and D- and L-α-hydroxy analogs of Leucine, Isoleucine and Valine by chicks and rats. J Nutr. 1982 Oct; 112(10):1929-39). This reamination will act to reduce accumulation of nitrogen in working cells, which will result in a reduction in the occurrence of delayed onset muscular soreness.

Administration of about 1.5 g of HICA daily after intense exercise for a period of 42 days (Karila T, Seppala T. α-Hydroxyisocaproic acid (HICA)—a Leucine metabolite for muscle recovery following exercise. www.elmomed.com) resulted in a statistically significant increase in total lean soft tissue mass. Additionally it was noted that subjects receiving HICA experienced little to no delayed onset muscle soreness. It is likely that this elimination of delayed onset muscle soreness is a result of inhibition of metalloproteinases, which are responsible for degradation of the extracellular matrix during tissue remodeling.

Additionally in high catabolic states, such as those induced by intensive exercise, both α-keto acids and α-hydroxy acid metabolites of branched chain amino acids may be oxidized for energy instead of the branched chain amino acids themselves (Staten M A, Bier D M, Matthews D E. Regulation of valine metabolism in man: a stable isotope study. Am J Clin Nutr. 1984 December; 40(6):1224-34). Using the deaminated metabolites, e.g. HICA, over the aminated forms, e.g. Leucine, will act to attenuate ammonia accumulation in working muscle. Also, α-hydroxy acid analogues, like HICA, can be reaminated to yield the corresponding branched chain amino acids (Hoffer L J, Taveroff A, Robitaille L, Mame O A, Reimer M L. Alpha-keto and alpha-hydroxy branched-chain acid interrelationships in normal humans. J Nutr. 1993 September; 123(9):1513-21). Thus, oral administration of at least one α-hydroxy branched-chain amino acid metabolite will act to increase levels of the corresponding branched-chain amino acid present in skeletal muscle.

Leucine is able to stimulate protein synthesis and inhibit protein breakdown (Tischler M E, Desautels M, Goldberg A L. Does Leucine, leucyl-tRNA, or some metabolite of Leucine regulate protein synthesis and degradation in skeletal and cardiac muscle? J Biol Chem. 1982 February. 25; 257(4): 1613-21), both of which would be favorable in working muscle as they result in increased skeletal muscle growth and decreased recovery time.

It is herein understood by the inventors that oral administration of HICA will act to increase muscular concentrations of Leucine by acting as a substitute for Leucine in catabolism for energy as well as potentially being reaminated to form Leucine. Increased levels of Leucine will stimulate protein synthesis and inhibit protein breakdown, thereby inducing an anabolically-favorable state for the cell. Additionally, it is herein understood by the inventors that oral administration of HIMVA and HIVA will act to increase muscular concentrations of Isoleucine and Valine, respectively, by at least the mechanisms discussed above.

In an embodiment of the present invention, which is set forth in greater detail in the examples below, the nutritional composition comprises α-hydroxyisocaproic acid. A serving of the nutritional composition comprises from about 0.00001 g to about 0.75 g of α-hydroxyisocaproic acid.

In a further embodiment of the present invention, which is set forth in greater detail in the examples below, the nutritional composition comprises α-hydroxy-β-methylvaleric acid. A serving of the nutritional composition comprises from about 0.00001 g to about 0.75 g of α-hydroxy-β-methylvaleric acid.

In an embodiment of the present invention, which is set forth in greater detail in the examples below, the nutritional composition comprises α-hydroxy-isovaleric acid. A serving of the nutritional composition comprises from about 0.00001 g to about 0.75 g of α-hydroxy-isovaleric acid.

In various embodiments of the present invention, which are set forth in greater detail in the examples below, the nutritional supplement comprises ethyl pyruvate and at least one α-hydroxy branched-chain amino acid metabolite. The nutritional supplement is provided in any acceptable and suitable oral dosage form as known in the art. A synergistic anabolically-favorable state for the cell, via substantially simultaneously maintaining physiological pH levels and increasing cellular concentrations of branched-chain amino acids, is induced and carried out in an individual by administration of the composition of the present invention.

The nutritional supplement of the present invention may be administered in a dosage form having controlled release characteristics, e.g. time-release. Furthermore, the controlled release may be in forms such as a delayed release of active constituents, gradual release of active constituents, or prolonged release of active constituents. Such active constituent release strategies extend the period of bioavailability or target a specific time window for optimal bioavailability. Advantageously the nutritional supplement may be administered in the form of a multi-compartment capsule which combines both immediate release and time-release characteristics. Individual components of the nutritional supplement may be contained in differential compartments of such a capsule such that specific components are released rapidly while others are time-dependently released. Alternatively, a uniform mix of the various components of the present invention may be divided into both immediate release and time-release compartments to provide a multi-phasic release profile.

While not wishing to be bound by theory, the present invention is comprised of components which act to attenuate acidosis in working muscle by increasing the conversion of pyruvate to lactate, which consumes free cytostolic protons ($H^+$). Additionally, increased concentrations of lactate, which result, will increase the co-transport of lactate and cytostolic $H^+$ into the mitochondria, thereby decreasing the concentration of cytostolic protons and increasing substrates in the mitochondria which are available to fuel the citric acid cycle. Both of the aforementioned mechanisms will enhance the buffering ability of the cell. Since decreased cellular pH has been linked to cell damage (Bevilacqua L, Ramsey J J, Haqopian K, Weindruch R, Harper M E. Effects of short- and medium-term calorie restriction on muscle mitochondrial proton leak and reactive oxygen species production. Am J Physiol Endocrinol Metab. 2004 May; 286(5):E852-61 (Abstract)) leading to degradation, attenuation of pH decreases would be anti-catabolic and as such would act to induce an anabolically-favorable state for the cell.

Additionally, the present invention comprises components which have been shown to increase levels of branched-chain amino acids. It is herein understood by the inventors that inclusion of HICA in the nutritional supplement will act to increase muscular concentrations of Leucine by acting as a substitute for Leucine in catabolism for energy as well as potentially being reaminated to form Leucine. Increased levels of Leucine will stimulate protein synthesis and inhibit protein breakdown, thereby inducing an anabolically-favorable state for the cell.

Further to the aforementioned functions, it is herein understood that administration of ethyl pyruvate and HICA concomitantly in a single serving of the nutritional supplement act substantially simultaneously to induce an anabolically-favorable state in cells. Administration of ethyl pyruvate increases cellular concentrations of lactate which are preferentially utilized for energy, thereby sparing the concentrations of BCAA, such as Leucine. In a manner similar to ethyl pyruvate, HICA will spare the concentrations of BCAA, however, HICA has the additional capability of conversion to Leucine, thereby not only conserving Leucine, but also acting to increase the concentrations of Leucine. Therefore, administration of ethyl pyruvate and HICA together will conserve and increase Leucine concentrations, wherein an anabolically-favorable state for the cell is induced.

Additional embodiments of the present invention may also include portions of the composition as fine-milled ingredients. U.S. Non-Provisional patent application Ser. No. 11/709,526 entitled "Method for Increasing the Rate and Consistency of Bioavailability of Supplemental Dietary Ingredients" filed Feb. 21, 2007, which is herein fully incorporated by reference, discloses a method of increasing the rate of bioavailability following oral administration of components comprising supplemental dietary compositions by the process of particle-milling.

Furthermore, additional embodiments of the present invention may be incorporated into specific controlled-release solid dosage forms. U.S. Non-Provisional patent application Ser. No. 11/709,525 entitled "Method for a Supplemental Dietary Composition Having a Multi-Phase Dissolution Profile" filed Feb. 21, 2007, which is herein fully incorporated by reference, discloses a method of achieving a solid oral dosage form with multiple dissolution characteristics for the release of active ingredients.

According to various embodiments of the present invention, the nutritional supplement may be consumed in any form. For instance, the dosage form of the nutritional supplement may be provided as, e.g., a powder beverage mix, a liquid beverage, a ready-to-eat bar or drink product, a capsule, a liquid capsule, a tablet, a caplet, or as a dietary gel. The preferred dosage forms of the present invention are as a caplet or as a liquid capsule.

Furthermore, the dosage form of the nutritional supplement may be provided in accordance with customary processing techniques for herbal and nutritional supplements in any of the forms mentioned above. Additionally, the nutritional supplement set forth in the example embodiment herein disclosed may contain any appropriate number and type of excipients, as is well known in the art. By way of ingestion of the composition of the present invention, a method for inducing an anabolically-favorable state for the cell by substantially simultaneously maintaining blood and muscle physiological pH levels and increasing cellular concentrations of Leucine, is provided. The method of the present invention comprises at least the step of administering to an individual a therapeutically acceptable amount of the composition of the present invention.

Although the following example illustrates the practice of the present invention in one of its embodiments, the example should not be construed as limiting the scope of the invention. Other embodiments will be apparent to one of skill in the art from consideration of the specifications and example.

EXAMPLES

Example 1

A nutritional supplement comprising the following ingredients per serving is prepared for consumption as a caplet three times daily prior to meals:
from about 0.0001 g to about 0.75 g of ethyl pyruvate and from about 0.00001 g to about 0.75 g of α-hydroxyisocaproic acid (HICA).

Example 2

A nutritional supplement comprising the following ingredients per serving is prepared for consumption as a caplet three times daily prior to meals:
about 0.001 g of ethyl pyruvate and about 0.0001 g of α-hydroxyisocaproic acid (H ICA).

Example 3

A nutritional supplement comprising the following ingredients per serving is prepared for consumption as a time-release multi-compartmented capsule twice daily prior to meals, preferably once before the first meal and once before the last meal of the day:
about 0.005 g of ethyl pyruvate and about 0.0005 g of α-hydroxyisocaproic acid (HICA).

Example 4

A nutritional supplement comprising the following ingredients per serving is prepared for consumption as a capsule to be taken once daily prior to exercise:
about 0.01 g of ethyl pyruvate, about 0.001 g of α-hydroxyisocaproic acid (HICA), about 0.001 g of α-hydroxy-β-methylvaleric acid (HIMVA), and about 0.001 g of α-hydroxy-isovaleric acid (HIVA).

Example 5

A nutritional supplement comprising the following ingredients per serving is prepared for consumption as a caplet to be taken once daily following exercise:
about 0.01 g of ethyl pyruvate, about 0.001 g of α-hydroxyisocaproic acid (HICA), about 0.001 g of α-hydroxy-β-methylvaleric acid (HIMVA), and about 0.001 g of α-hydroxy-isovaleric acid (HIVA).

Extensions and Alternatives

In the foregoing specification, the invention has been described with a specific embodiment thereof; however, it will be evident that various modifications and changes may be made thereto without departing from the broader spirit and scope of the invention.

What is claimed:

1. A composition for causing an anabolically-favorable state for muscle in a mammal, comprising ethyl pyruvate and at least one α-hydroxy branched-chain amino acid metabolite.

2. The composition of claim 1, wherein the α-hydroxy branched-chain amino acid metabolite is selected from the group consisting of α-hydroxyisocaproic acid, α-hydroxy-β-methylvaleric acid, and α-hydroxy-isovaleric acid.

3. The composition of claim 1 wherein the ethyl pyruvate and the α-hydroxy branched-chain amino acid metabolite are part of a solid oral dosage form having a multi-phasic rate of dissolution.

4. The composition of claim 3 wherein said multi-phasic rate of dissolution comprises a first-phase and a second-phase; whereby said first-phase has a first rate of dissolution said second-phase has a second rate of dissolution.

5. The composition of claim 4, wherein the multi-phasic rate of dissolution provides a time-release mechanism.

6. The composition of claim 4, further comprising a third-phase, whereby said third-phase has a third rate of dissolution.

7. The composition of claim 5, wherein the multi-phasic rate of dissolution provides a time-release mechanism.

8. A method for causing an anabolically-favorable state of muscle in a mammal, comprising at least the step of administering to the mammal a composition comprising ethyl pyruvate and at least one α-hydroxy branched-chain amino acid metabolite.

9. The method of claim 8, wherein the .alpha.-hydroxy branched-chain amino acid metabolite is selected from the group consisting of α-hydroxyisocaproic acid, α-hydroxy-β-methylvaleric acid, and α-hydroxy-isovaleric acid.

10. The method of claim 8 wherein the ethyl pyruvate and the α-hydroxyisocaproic acid are part of a solid oral dosage form having a multi-phasic rate of dissolution.

11. The method of claim 10 wherein said multi-phasic rate of dissolution comprises a first-phase and a second-phase; whereby said first-phase has a first rate of dissolution said second-phase has a second rate of dissolution.

12. The method of claim 10, wherein the multi-phasic rate of dissolution provides a time-release mechanism.

13. The method of claim 11, further comprising a third-phase, whereby said third-phase has a third rate of dissolution.

14. The method of claim 13, wherein the multi-phasic rate of dissolution provides a time-release mechanism.

\* \* \* \* \*